US012722240B2

(12) United States Patent
Tsuji et al.

(10) Patent No.: US 12,722,240 B2
(45) Date of Patent: Sep. 1, 2026

(54) CUTTING MACHINING APPARATUS

(71) Applicant: NISSIN FULFIL CO., LTD., Kyoto (JP)

(72) Inventors: Hidekazu Tsuji, Kyoto (JP); Shuhei Muraoka, Kyoto (JP); Ryosuke Yamazoe, Kyoto (JP); Kenji Inoue, Kyoto (JP); Koji Tanaka, Kyoto (JP); Akira Nishikohri, Kyoto (JP)

(73) Assignee: NISSIN FULFIL CO., LTD., Kyoto (JP)

( * ) Notice: Subject to any disclaimer, the term of this patent is extended or adjusted under 35 U.S.C. 154(b) by 328 days.

(21) Appl. No.: 18/707,346

(22) PCT Filed: Nov. 4, 2022

(86) PCT No.: PCT/JP2022/041231
§ 371 (c)(1),
(2) Date: May 3, 2024

(87) PCT Pub. No.: WO2023/080212
PCT Pub. Date: May 11, 2023

(65) Prior Publication Data

US 2026/0158604 A1 Jun. 11, 2026

(30) Foreign Application Priority Data

Nov. 5, 2021 (JP) ................................ 2021-180982

(51) Int. Cl.

| | |
|---|---|
| ***B23Q 11/08*** | (2006.01) |
| *A61B 17/16* | (2006.01) |
| *A61F 2/46* | (2006.01) |

(52) U.S. Cl.
CPC ...... *B23Q 11/0891* (2013.01); *B23Q 11/0883* (2013.01); *A61B 2017/1602* (2013.01);
(Continued)

(58) Field of Classification Search
CPC ... B23Q 11/08; B23Q 11/0816; B23Q 11/085; B23Q 11/0883; B23Q 11/0891; A61B 2017/1602; A61F 2002/4645
See application file for complete search history.

(56) References Cited

U.S. PATENT DOCUMENTS

| | | | | |
|---|---|---|---|---|
| 5,607,269 | A * | 3/1997 | Dowd ................ | B23Q 11/0825 29/DIG. 56 |
| 2017/0304908 | A1 | 10/2017 | Travert | |
| 2020/0262018 | A1* | 8/2020 | DeSoutter .......... | A61B 17/8863 |

FOREIGN PATENT DOCUMENTS

| | | |
|---|---|---|
| JP | S62-074943 U | 5/1987 |
| JP | 2004-106129 A | 4/2004 |

(Continued)

OTHER PUBLICATIONS

International Search Report and Written Opinion; International Application No. PCT/JP2022/041231; Jan. 10, 2023.

*Primary Examiner* — Matthew P Travers
(74) *Attorney, Agent, or Firm* — Ohlandt, Greeley and Perle, L.L.P.

(57) ABSTRACT

A cutting machining device includes: a head; a holding unit that holds a workpiece; an interior case that has a first opening through which the holding unit is inserted and a second opening through which the head is inserted, a workpiece holding unit in the holding unit and the tool held by the head being disposed inside the interior case; a first cover that blocks between the holding unit and an outer circumferential portion of the first opening in the interior case; and a second cover that is formed of a soft material, and blocks between the head and an outer circumferential portion of the second opening in the interior case.

9 Claims, 6 Drawing Sheets

(52) U.S. Cl.
CPC ... *A61F 2002/4645* (2013.01); *B23Q 11/0816* (2013.01); *B23Q 11/085* (2013.01)

(56) References Cited

FOREIGN PATENT DOCUMENTS

| | | | |
|---|---|---|---|
| JP | 2011-5587 | A | 1/2011 |
| JP | 2017-222019 | A | 12/2017 |
| JP | 2019-135071 | A | 8/2019 |

* cited by examiner

CUTTING MACHINING APPARATUS

CROSS-REFERENCE TO RELATED APPLICATIONS

This application is a national stage application, filed under 35 U.S.C. § 371, of International Patent Application No. PCT/JP 2022/041232 filed Nov. 4, 2022, which claims the benefit of Japanese Patent Application No. JP 2021-180982 filed Nov. 5, 2021, the entire disclosures of which are incorporated herein by reference for all purposes.

TECHNICAL FIELD

The present disclosure relates to a cutting machining device.

BACKGROUND ART

A screw for bonding bones together is manufactured by performing cutting machining on a bone fragment acquired by cutting a bone of a patient himself/herself, and a broken bone portion of the patient is bonded by the screw. Thus, an attempt is being made to make a further operation for removing the screw after the broken bone portion adheres unnecessarily and to greatly reduce a load on the patient. In this case, the bone fragment is required to be subjected to cutting machining with high accuracy. A machining center used in such highly accurate cutting machining is proposed (for example, see Patent Literature 1).

CITATION LIST

Patent Literature

Patent Literature 1: Utility Model No. S62-74943

SUMMARY OF INVENTION

Technical Problem

When a screw is manufactured by cutting machining, foreign matter present in a region where the screw is manufactured needs to be reduced as much as possible from a viewpoint of preventing an infectious disease of a patient due to various germs adhering to the manufactured screw. However, in the machining center described in Patent Literature 1, a machining region is exposed to the outside, and thus there is a risk that a screw may be contaminated by foreign matter present around a bone fragment being a machining target.

The present disclosure has been made in view of the reasons described above, and has an objective to provide a cutting machining device that can increase a degree of cleanliness of a region where cutting machining is performed.

Solution to Problem

In order to achieve the objective described above, a cutting machining device according to the present disclosure includes:

a head to which a tool is fixed;

a holding unit that is disposed to face the head, and holds a workpiece;

an interior case that has a box shape, and has, in a surrounding wall, a first opening through which the holding unit is inserted and a second opening through which the head is inserted, at least a portion in the holding unit for holding the workpiece and the tool held by the head being disposed inside the interior case;

a holding unit cover that has a bottomed tubular shape, has, in a side wall, a holding unit insertion hole through which a portion in the holding unit for holding the workpiece is inserted, and is mounted on the holding unit while the portion in the holding unit for holding the workpiece is inserted through the holding unit insertion hole;

a head cover that has a bottomed tubular shape, has, in a bottom wall, a head insertion hole through which a portion in the head for holding the tool is inserted, and is mounted on the head while the portion in the head for holding the tool is inserted through the head insertion hole;

a first cover that is formed of a soft material, and blocks between the holding unit cover and an outer circumferential portion of the first opening in the interior case; and a second cover that is formed of a soft material, and blocks between the head cover and an outer circumferential portion of the second opening in the interior case.

Advantageous Effects of Invention

According to the present disclosure, the interior case having, in the surrounding wall, the first opening through which the holding unit is inserted and the second opening through which the head is inserted is included, and at least the portion in the holding unit for holding the workpiece and the tool held by the head are disposed inside the interior case. Then, the first cover blocks between the holding unit cover and the outer circumferential portion of the first opening in the interior case, and the second cover blocks between the head cover and the outer circumferential portion of the second opening in the interior case. In this way, a region where cutting machining is performed can be formed inside the interior case separately from the outside of the interior case, and thus entry of foreign matter present outside the interior case into the region where cutting machining is performed can be suppressed, and a degree of cleanliness of the region where cutting machining is performed can be increased.

DESCRIPTION OF EMBODIMENTS

Hereinafter, a cutting machining device according to the embodiments of the present disclosure is described with reference to drawings. The cutting machining device according to the present embodiment includes: a head to which a tool is fixed; a holding unit that is disposed to face the head, and holds a workpiece; an interior case that has a box shape, and has, in a surrounding wall, a first opening through which the holding unit is inserted and a second opening through which the head is inserted, at least a portion in the holding unit for holding the workpiece and the tool held by the head being disposed inside the interior case; a holding unit cover that has a bottomed tubular shape, has, in a side wall, a holding unit insertion hole through which a portion in the holding unit for holding the workpiece is inserted, and is mounted on the holding unit while the portion in the holding unit for holding the workpiece is inserted through the holding unit insertion hole; a head cover that has a bottomed tubular shape, has, in a bottom wall, a head insertion hole through which a portion in the head for holding the tool is inserted, and is mounted on the head while the portion in the head for holding the tool is inserted through the head insertion hole; a first cover that is formed of a soft material, and blocks between the holding unit and an outer circumferential portion of the first opening in the interior case; and a second cover that is formed of a soft material, and blocks between the head and an outer circumferential portion of the second opening in the interior case.

Figure 1:
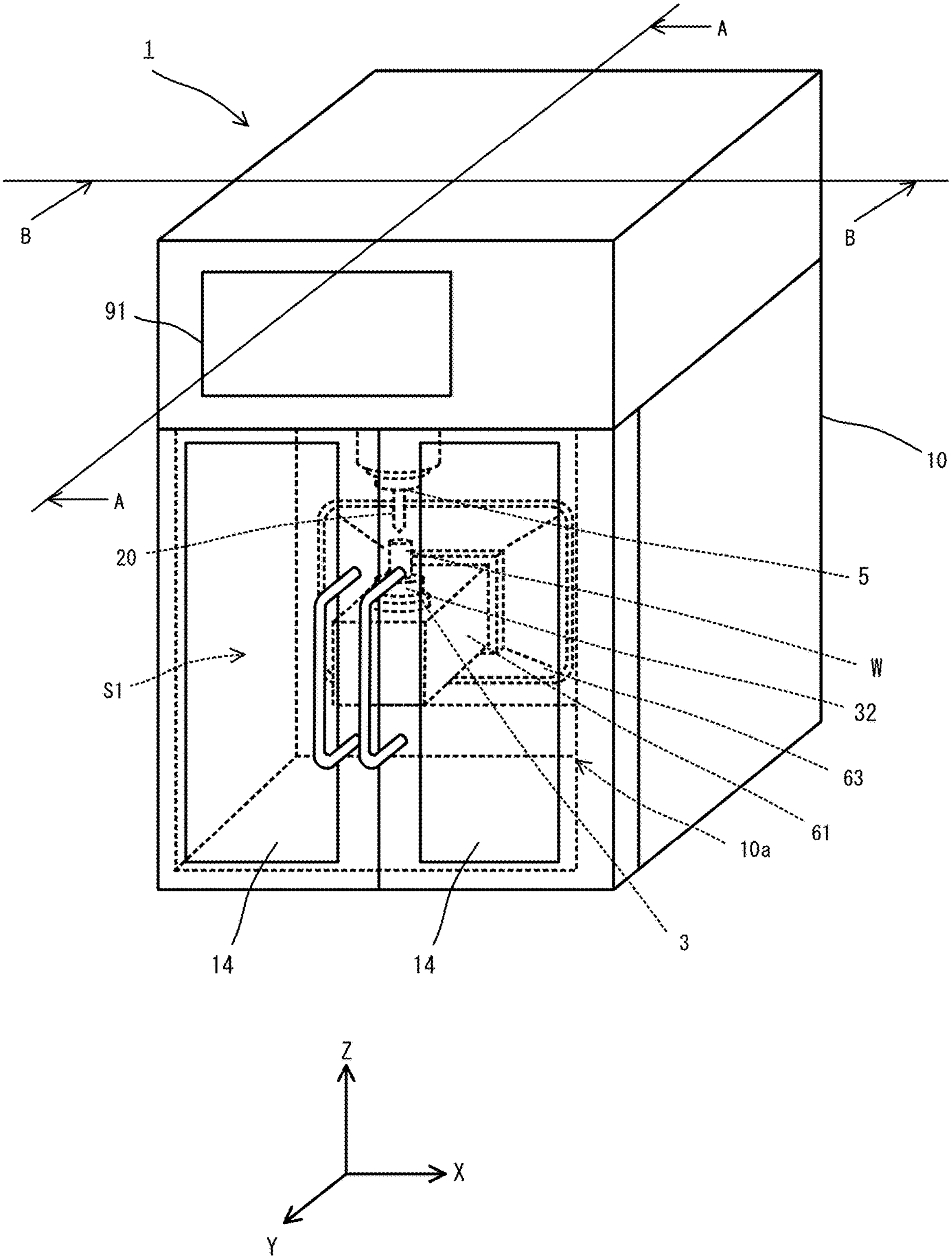
FIG. 1 is a schematic diagram of a cutting machining device according to an embodiment of the present disclosure.
Figure 2:
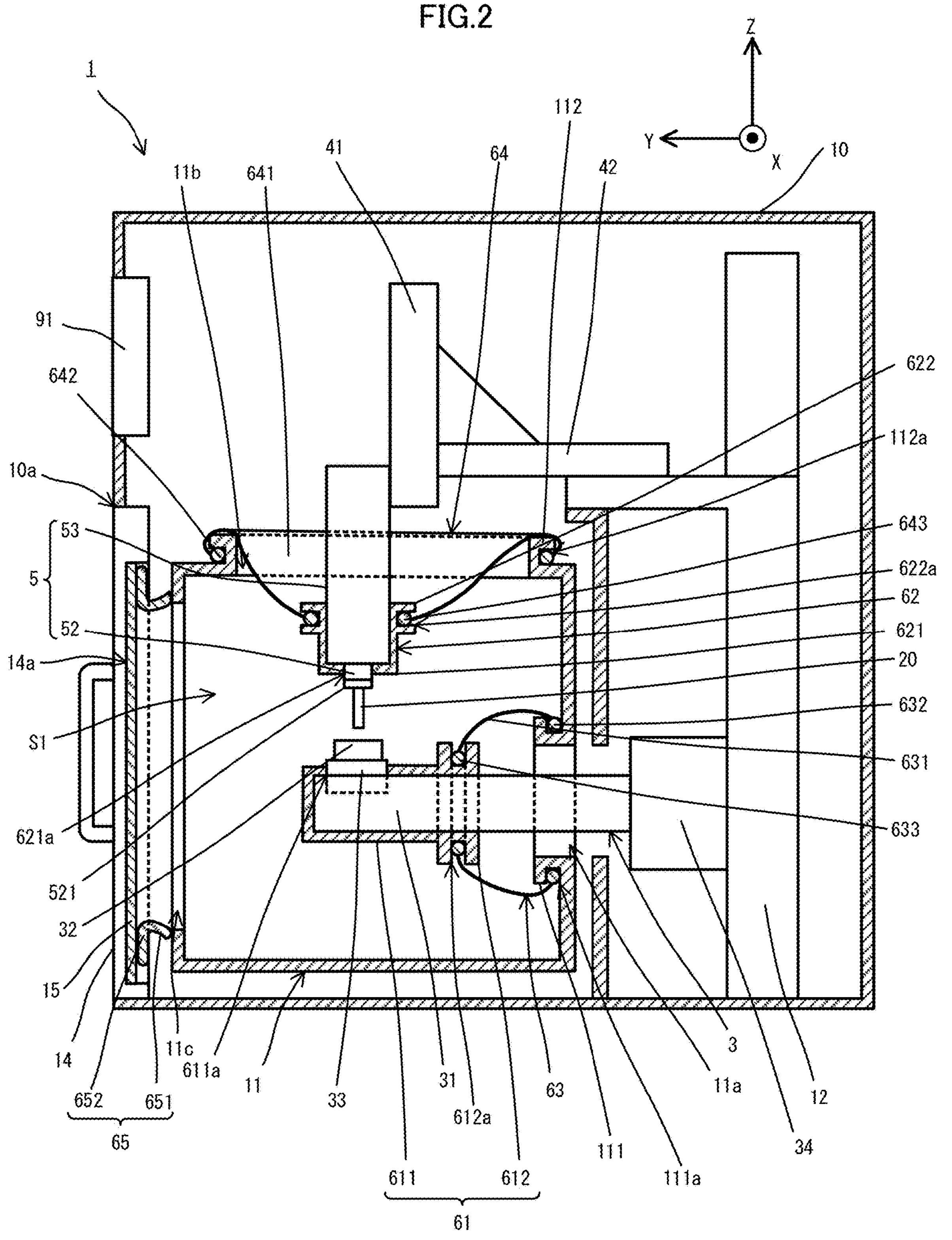
FIG. 2 is an arrow cross-sectional view of the cutting machining device according to the embodiment taken along an A-A line in FIG. 1.
Figure 3:
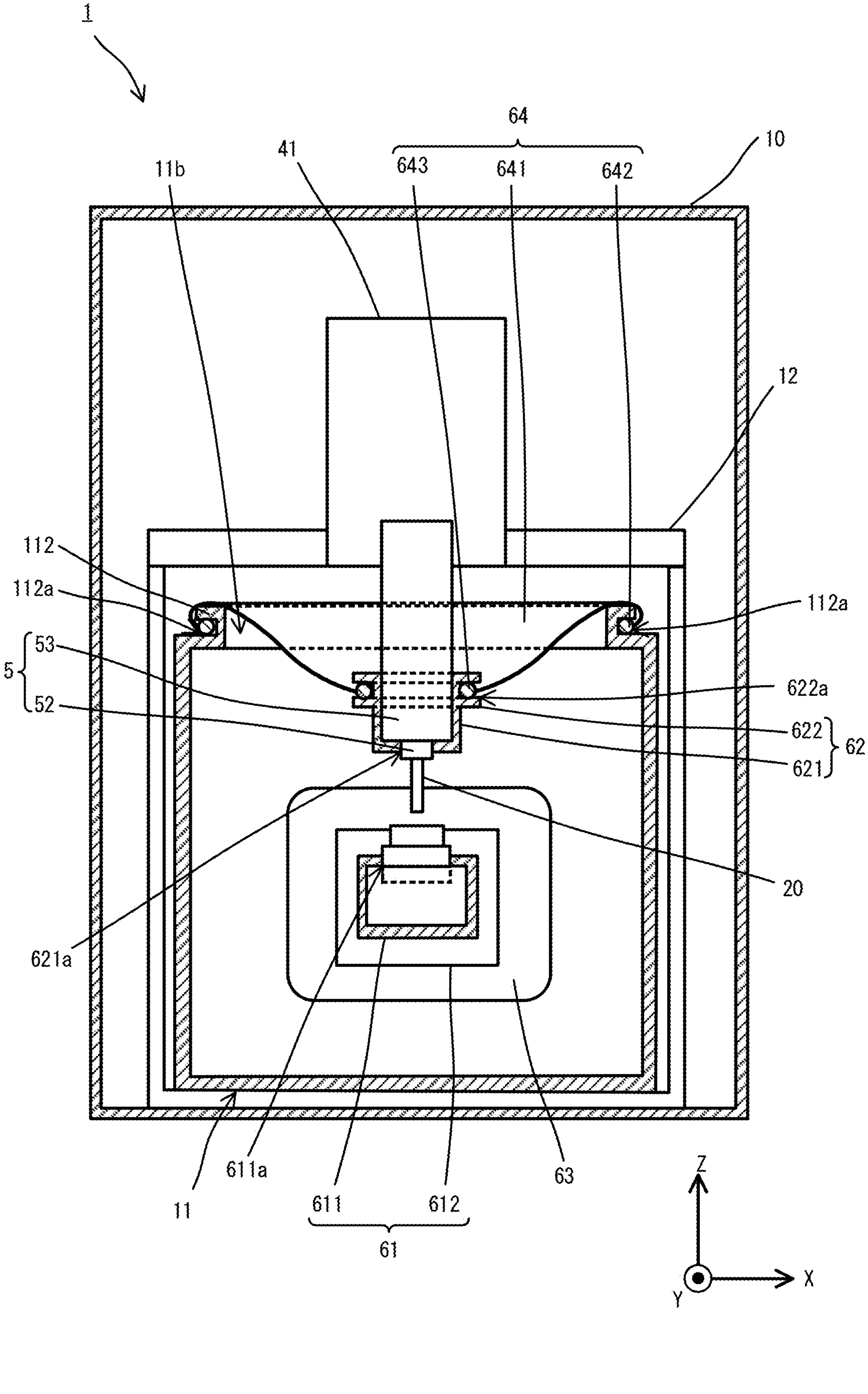
FIG. 3 is an arrow cross-sectional view of the cutting machining device according to the embodiment taken along a B-B line in FIG. 1.

As illustrated in FIG. 1, a cutting machining device 1 according to the present embodiment includes a head 5 to which a tool 20 is fixed, a holding unit 3 that is disposed to face the head 5, and holds a workpiece W, and a control panel 91 that controls a movement of the head 5 and the holding unit 3. Further, the cutting machining device 1 includes a housing 10 having a rectangular box shape and having a window portion 10*a* for putting in and taking out the workpiece W in a side wall on a +Y direction side, and two doors 14 attached to a surrounding wall of the housing 10. Furthermore, as illustrated in FIGS. 2 and 3, the cutting machining device 1 includes a protective panel 15 disposed inside the doors 14, an interior case 11 that has a box shape and is disposed inside the housing 10, a holding unit cover 61, a head cover 62, a first cover 63, a second cover 64, and a gasket 65. Further, the cutting machining device 1 includes a raising and lowering driver 41 that raises and lowers the head 5 in a vertical direction, a horizontal driver 42 that drives the head 5 along an X-axis direction and a Y-axis direction, and a support stage 12 that collectively supports the head 5, the raising and lowering driver 41, and the horizontal driver 42. The housing 10 is formed of, for example, metal, and, as illustrated in FIG. 2, the head 5, the holding unit 3, the interior case 11, the first cover 63, and the second cover 64 are housed inside the housing 10.

The two doors 14 are each attached to an outer circumferential portion of the window portion 10*a* in the surrounding wall of the housing 10 in such a way as to be freely opened and closed, and can be brought into a close state of covering the window portion 10*a* of the housing 10 from the +Y direction side and an open state of leaving the window portion 10*a* open. Further, a first recessed portion 14*a* in which the protective panel 15 having a rectangular plate shape is fit is formed on a surface side of the doors 14 facing the inside of the housing 10. The protective panel 15 is disposed in such a way as to cover the window portion of the housing 10 between the interior case 11 and the doors 14 while the protective panel 15 is fit in the first recessed portion 14*a* of the doors 14. The doors 14 and the protective panel 15 are each formed of, for example, transparent polycarbonate. In this case, a user of the cutting machining device 1 can observe the workpiece W disposed in a machining region S1 where cutting machining is performed inside the housing 10 with the doors 14 in the close state while the protective panel 15 is fit in the recessed portion of the doors 14, and can also appropriately perform sterilization treatment using ethylene oxide gas on the doors 14, which is preferable from a viewpoint of maintaining the doors 14 in a clean state. Further, the housing 10 includes a locking portion (not illustrated) that locks the interior case 11 when the interior case 11 is disposed in a preset fixed position inside the housing 10. For example, the locking portion includes an engagement recessed portion engaged with a protrusion (not illustrated) provided on an outer wall of the interior case 11 described below.

The head 5 includes a main rotating shaft 52 that is long and is provided with, on one end portion in a longitudinal direction, a tool holding portion 521 that holds the tool 20, a head main body 53 that houses a part of the main rotating shaft 52, and a main shaft driving motor (not illustrated) that is built in the head main body 53 and rotates the main rotating shaft 52 about a central axis along the longitudinal direction. The tool holding portion 521 includes a chuck (not illustrated). The raising and lowering driver 41 includes a rail (not illustrated) extending along a Z-axis direction, a slider (not illustrated) held to slide freely on the rail, a ball screw (not illustrated) screwed on a nut portion (not illustrated) disposed along the Z-axis direction and provided on a part of the slider, and a motor coupled to the ball screw. Then, the raising and lowering driver 41 raises and lowers, along the Z-axis direction, the slider and the head 5 fixed to the slider by rotating the ball screw by the motor. Further, the horizontal driver 42 moves the head 5 held by the raising and lowering driver 41 along the X-axis direction or the Y-axis direction by moving the raising and lowering driver 41 along the X-axis direction or the Y-axis direction.

The holding unit 3 includes a workpiece holding unit 32 that holds the workpiece W, a holding portion driver 33 that rotates and drives the workpiece holding unit 32, a unit main body 31 that has a rectangular box shape and houses a part of the holding portion driver 33, and a main body driver 34 that drives the unit main body 31. The main body driver 34 is supported by the support stage 12. The main body driver 34 rotates the entire unit main body 31 about a rotation axis extending in the longitudinal direction of the unit main body 31. Further, the holding portion driver 33 rotates the workpiece holding unit 32 about a rotation axis extending in a direction orthogonal to the longitudinal direction of the unit main body 31. The workpiece holding unit 32 is, for example, a chuck that sandwiches a base end portion of the long workpiece W.

The interior case 11 has a box shape, and has, in the surrounding wall, a first opening 11*a* through which the holding unit 3 is inserted and a second opening 11*b* through which the head 5 is inserted. The interior case 11 is formed of, for example, metal. The workpiece holding unit 32 in the holding unit 3 and the tool 20 held by the head 5 are disposed inside the interior case 11, and the machining region S1 described above is formed inside the interior case 11. Further, the interior case 11 has a third opening 11*c* having a planar rectangular shape in a portion in the surrounding wall of the interior case 11 facing the window portion 10*a* of the housing 10 while the interior case 11 is disposed in the housing 10. Furthermore, the interior case 11 includes a first rib 111 that has a tubular shape, and protrudes from an outer circumferential portion of the first opening 11*a* in the surrounding wall of the interior case 11 toward the inside of the interior case 11, and a second rib 112 that has a tubular shape, and protrudes from an outer circumferential portion of the second opening 11_b_ in the surrounding wall of the interior case 11 toward the outside of the interior case 11. An outer wall of the first rib 111 is provided with a third groove 111_a_ extending along a circumferential direction of the first rib 111. Further, an outer wall of the second rib 112 is also provided with a fourth groove 112_a_ extending along a circumferential direction of the second rib 112. The third groove 111_a_ and the fourth groove 112_a_ are formed by, for example, bending tip portions of the first rib 111 and the second rib 111 to the outside. Further, the protrusion (not illustrated) is provided on a portion in the surrounding wall of the interior case 11 facing the engagement recessed portion of the above-described locking portion provided in the housing 10. Then, when the interior case 11 is inserted into the housing 10 from the window portion 10_a_ of the housing 10 and moved to the above-described fixed position, the protrusion is engaged with the engagement recessed portion of the housing 10 and locked in the housing 10. On the other hand, when force having preset magnitude acts on the window portion 10_a_ from the fixed position while the interior case 11 is locked in the above-described fixed position in the housing 10, the state where the protrusion is engaged with the engagement recessed portion is released. Then, the interior case 11 can move toward the window portion 10_a_ with respect to the housing 10. In this way, the interior case 11 is freely attachable and detachable with respect to the housing 10.

The holding unit cover 61 includes a holding unit cover main body 611 having a bottomed square tubular shape, and a first outer flange portion 612 protruding from the holding unit cover main body 611 in a direction away from a tubular axis of the holding unit cover main body 611 in a direction orthogonal to a tubular axis direction of the holding unit cover main body 611. The holding unit cover 61 is formed of, for example, metal, and can be subjected to sterilization using, for example, ethylene oxide gas. A first holding unit insertion hole 611_a_ through which a part of the workpiece holding unit 32 and the holding portion driver 33 in the unit main body 31 of the holding unit 3 can be inserted is provided in a side wall of the holding unit cover main body 611. The first outer flange portion 612 is located closer to a side opposite to a bottom wall side than the first holding unit insertion hole 611_a_ in the outside of the side wall of the holding unit cover main body 611, i.e., located on an end portion on the side opposite to the bottom wall side. Further, a first groove 612_a_ extending around the tubular axis of the holding unit cover main body 611 is formed in a circumferential surface of the first outer flange portion 612. The holding unit cover 61 is mounted on the holding unit 3 while a part of the workpiece holding unit 32 and the holding portion driver 33 of the holding unit 3 is inserted through the first holding unit insertion hole 611_a_.

The head cover 62 includes a head cover main body 621 having a bottomed tubular shape, and a second outer flange portion 622 protruding from the head cover main body 612 in a direction away from a tubular axis of the head cover main body 621 in a direction orthogonal to a tubular axis direction of the head cover main body 621. The head cover 62 is also formed of, for example, metal, and can also be subjected to sterilization using, for example, ethylene oxide gas. A head insertion hole 621_a_ through which the main rotating shaft 52 in the head 5 that holds the tool 20 can be inserted is provided in a bottom wall of the head cover main body 621. The second outer flange portion 622 is located on an end portion on a side opposite to a bottom wall side in a side wall of the head cover main body 621. Further, a second groove 622_a_ extending around the tubular axis of the head cover main body 621 is formed in a circumferential surface of the second outer flange portion 622. The head cover 62 is mounted on the head main body 53 of the head 5 while the tool holding portion 521 of the main rotating shaft 52 of the head 5 is inserted through the head insertion hole 621_a_.

The first cover 63 blocks between the holding unit cover 61 and the outer circumferential portion of the first opening 11_a_ in the interior case 11. The first cover 63 is formed of a soft material such as a rubber thin film and a vinyl film, and is preferably able to be subjected to sterilization using, for example, ethylene oxide gas. The first cover 63 includes a first cover main body 631 formed in a tubular shape, a first interior case-side fixed portion 632, and a holding unit-side fixed portion 633. The interior case-side fixed portion 632 is formed in a ring shape and continuously integrally formed with an entire one end portion of the first cover main body 631 on a surrounding wall side of the interior case 11 in a tubular axis direction of the first cover main body 631. Further, the holding unit-side fixed portion 633 is formed in a ring shape and continuously integrally formed with an entire other end portion of the first cover main body 631 on the holding unit 3 side in the tubular axis direction of the first cover main body 631. The first interior case-side fixed portion 632 of the first cover 63 is fit in the third groove 111_a_ of the first rib 111 of the interior case 11, and the holding unit-side fixed portion 633 is fit in the first groove 612_a_ formed in the first outer flange portion 612 of the holding unit cover 61.

The second cover 64 blocks between the head cover 62 and the outer circumferential portion of the second opening 11_b_ in the interior case 11. The second cover 64 is also formed of a soft material such as a rubber thin film and a vinyl film, and is also preferably able to be subjected to sterilization using, for example, ethylene oxide gas. The second cover 64 includes a second cover main body 641 formed in a tubular shape, a second interior case-side fixed portion 642 that is formed in a ring shape and is continuously integrally formed with an entire one end portion of the second cover main body 641 on the one end portion in a tubular axis direction of the second cover main body 641, and a head-side fixed portion 643 that is formed in a ring shape and is continuously integrally formed with an entire other end portion of the second cover main body 641 on the other end portion in the tubular axis direction of the second cover main body 641. The second interior case-side fixed portion 642 of the second cover 64 is fit in the fourth groove 112_a_ of the second rib 112 of the interior case 11, and the head-side fixed portion 643 is fit in the second groove 622_a_ formed in the second outer flange portion 622 of the head cover 62.

The gasket 65 includes a gasket main body 651 formed in a planar rectangular ring shape, and a third outer flange portion 652 protruding from the other end portion of the gasket main body 651 in a direction away from a tubular axis of the gasket main body 651. The gasket main body 651 and the third outer flange portion 652 are continuously integrally formed of an elastic material such as silicone rubber, for example. In this case, sterilization treatment using ethylene oxide gas can be performed on the gasket 65, which is thus preferable from a viewpoint of maintaining the gasket 65 in a clean state. The third outer flange portion 652 is fixed to a surface of the protective panel 15 on a side opposite to the door 14 side. Then, when the doors 14 are brought into the close state while the protective panel 15 is fit in the first recessed portion 14_a_ of the doors 14, the entire end portion of the gasket main body 651 on a side opposite to the third outer flange portion 652 side is in close contact with an outer circumferential portion of the third opening 11*c* in the surrounding wall of the interior case 11.

Next, a method of using the cutting machining device 1 according to the present embodiment is described. Herein, a preparation method when cutting machining is performed on the workpiece W by using the cutting machining device 1 is described. First, the second interior case-side fixed portion 642 of the second cover 64 is fit in the entire fourth groove 112*a* formed in the outer wall of the second rib 112 of the interior case 11. Further, the head cover 62 is mounted on the head main body 53 of the head 5 by inserting the tool holding portion 521 side of the main rotating shaft 52 of the head 5 through the head insertion hole 621*a* of the head cover 62. At this time, an end portion of the main rotating shaft 52 on the tool holding portion 521 side protrudes to the outside of the head cover 62. Next, with the doors 14 in the open state, the interior case 11 to which the second cover 64 is attached is disposed in a preset fixed position inside the housing 10. At this time, the interior case 11 is in a state of being locked by the locking portion of the housing 10. Subsequently, the head-side fixed portion 643 of the second cover 64 is fit in the entire second groove 622*a* formed in the circumferential surface of the second outer flange portion 622 of the head cover 62.

Then, the holding unit-side fixed portion 633 of the first cover 63 is fit in the entire first groove 612*a* formed in the circumferential surface of the first outer flange portion 612 of the holding unit cover 61. Next, the holding unit cover 61 to which the first cover 63 is attached is mounted on the unit main body 31 of the holding unit 3. At this time, a part of the workpiece holding unit 32 and the holding portion driver 33 of the holding unit 3 is inserted through the first holding unit insertion hole 611*a* of the holding unit cover 61 and exposed to the outside of the holding unit cover 61. Subsequently, the first interior case-side fixed portion 632 of the first cover 63 is fit in the entire third groove 111*a* formed in the outer wall of the first rib 111 of the interior case 11. Then, after the protective panel 15 is disposed in such a way as to cover the window portion 10*a* of the housing 10, the doors 14 are brought into the close state, and then the protective panel 15 is fit in the first recessed portion 14*a* of the doors 14. In this way, preparation for performing cutting machining on the workpiece W is completed.

As described above, the cutting machining device 1 according to the present embodiment includes the interior case 11 having, in the surrounding wall, the first opening 11*a* through which the holding unit 3 is inserted and the second opening 11*b* through which the head 5 is inserted, and the workpiece holding unit 32 of the holding unit 3 and the tool 20 are disposed inside the interior case 11. Then, the first cover 63 blocks between the holding unit 3 and the outer circumferential portion of the first opening 11*a* in the interior case 11, and the second cover 64 blocks between the head 5 and the outer circumferential portion of the second opening 11*b* in the interior case 11. In this way, the machining region S1 separated from the outside of the interior case 11 can be formed inside the interior case 11, and thus entry of foreign matter present outside the interior case 11 into the machining region S1 can be suppressed, and a degree of cleanliness of the machining region S1 can be increased.

Further, when the protective panel 15 is disposed in such a way as to cover the window portion 10*a* of the housing 10 between the interior case 11 and the doors 14, and the doors 14 are in the close state, the entire end portion of the gasket 65 according to the present embodiment on the interior case 11 side is in close contact with the third opening 11*c* in the surrounding wall of the interior case 11. In this way, entry of foreign matter present outside the interior case 11 into the interior case 11 from a gap generated between the interior case 11 in the housing 10 and the doors 14 can be suppressed, and thus a degree of cleanliness of the machining region S1 inside the interior case 11 can be increased.

Furthermore, the interior case 11 according to the present embodiment is freely attachable and detachable with respect to the housing 10. In this way, the interior case 11 can be removed from the housing 10, and washed or subjected to disinfection treatment, and thus a degree of cleanliness inside the interior case 11 can be increased.

Further, the first cover 63 according to the present embodiment includes the first interior case-side fixed portion 632 that is formed in a ring shape, is continuously integrally formed with the entire one end portion in the tubular axis direction of the first cover main body 631, and is fit in the third groove 111*a* of the first rib 111 of the interior case 11, and the holding unit-side fixed portion 633 that is formed in a ring shape, is continuously integrally formed with the entire other end portion in the tubular axis direction of the first cover main body 631, and is fit in the first groove 612*a* of the first outer flange portion 612 of the holding unit cover 61. Further, the second cover 64 includes the second interior case-side fixed portion 642 that is formed in a ring shape, is continuously integrally formed with the entire one end portion in the tubular axis direction of the second cover main body 641, and is fit in the fourth groove 112*a* of the second rib 112 of the interior case 11, and the head-side fixed portion 643 that is formed in a ring shape, is continuously integrally formed with the entire other end portion in the tubular axis direction of the second cover main body 641, and is fit in the second groove 622*a* of the second outer flange portion 622 of the head cover 62. In this way, work for mounting the first cover 63 and the second cover 64 on the interior case 11 is facilitated, and thus there is an advantage that attaching/detaching of the interior case 11 with respect to the housing 10 is accordingly facilitated.

Further, the cutting machining device 1 according to the present embodiment is used together with, for example, a diagnostic imaging device, and a machining control information generation device that generates machining control information about the cutting machining device 1, based on shape information acquired by the diagnostic imaging device. In this case, in the cutting machining device 1, machining can be performed on the workpiece W, based on the appropriate machining control information that considers the shape information acquired by the diagnostic imaging device. Thus, for example, when the workpiece W is a bone extracted from a patient, the size of the workpiece W can be set to be an appropriate and minimum size, based on a result of an image diagnosis, and thus a load on the patient can be accordingly reduced.

Figure 4:
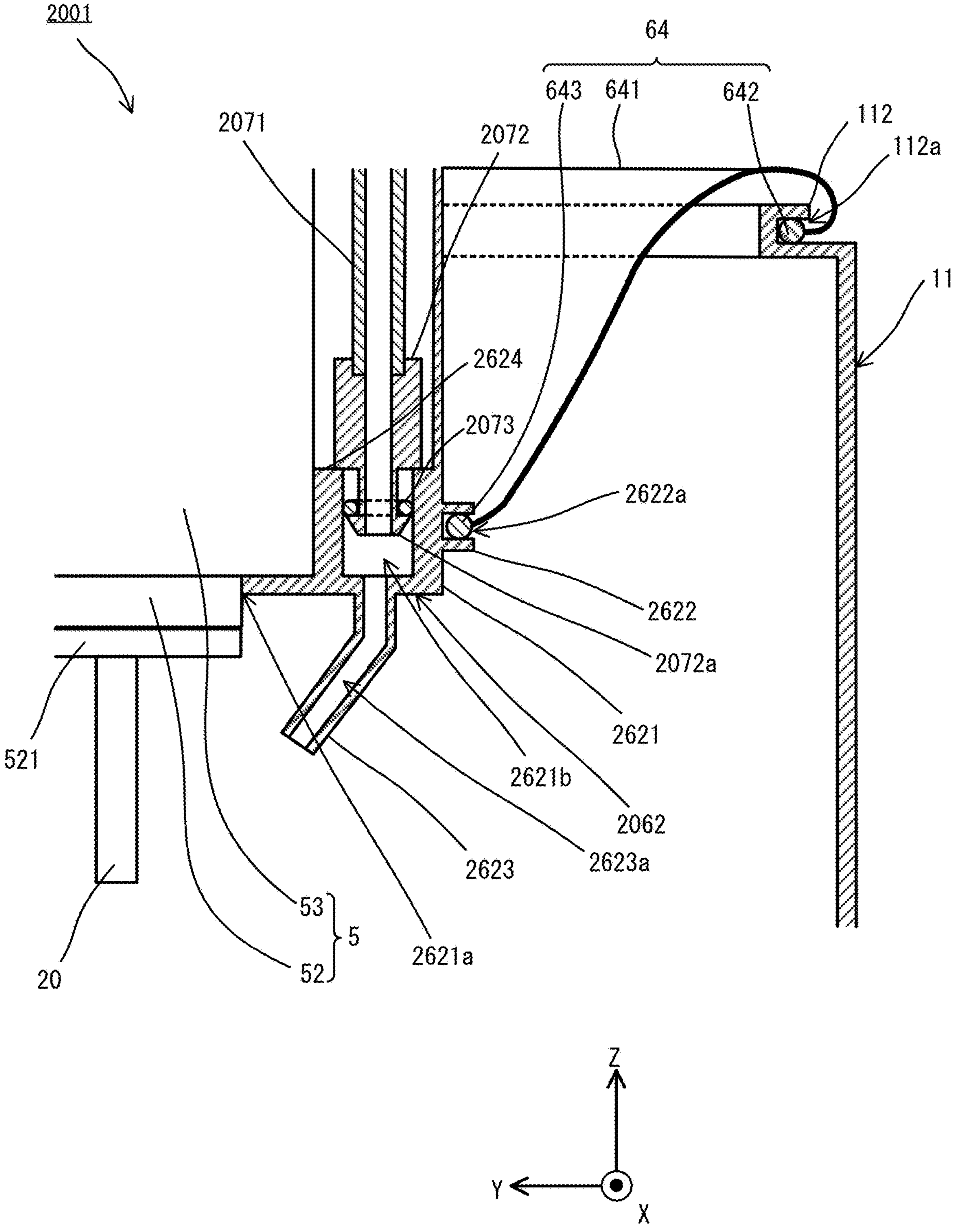
FIG. 4 is a cross-sectional view of a part of a cutting machining device according to a modification example.

Although the embodiments of the present disclosure have been described above, the present disclosure is not limited to the configuration of the embodiments described above. For example, as in a cutting machining device 2001 illustrated in FIG. 4, a head cover 2062 including a nozzle 2623 for ejecting gas for cooling the workpiece W toward the workpiece W may be included. The head cover 2062 includes a head cover main body 2621 having a bottomed tubular shape, and a fourth outer flange portion 2622 protruding from the head cover main body 2612 in a direction away from a tubular axis of the head cover main body 2621 in a direction orthogonal to a tubular axis direction of the head cover main body 2621. A second groove 2622*a* in which the head-side fixed portion 643 of the second cover 64 is fit is formed in the fourth outer flange portion 2622. The main rotating shaft 52 of the head 5 and the tool 20 are inserted through a head insertion hole 2621*a* provided in a bottom wall of the head cover main body 2621. The nozzle 2623 protrudes from a circumferential portion outside the bottom wall of the head cover main body 2621 to the −Z direction side, and a tip portion is bent in a direction approaching the tool 20 held by the head 5. Further, a step portion 2624 is formed along the circumferential portion of the bottom wall inside the head cover main body 2621, and a second recessed portion 2621 *b* communicating with an inside 2623*a* of the nozzle 2623 penetrates a portion of the step portion 2624 corresponding to the nozzle 2623. A tip portion 2072*a* of a gas connector 2072 mounted on a tip portion of a tube 2071 for carrying gas supplied from a gas supply source (not illustrated) is fit in the second recessed portion 2621*b*. A filter (not illustrated) for removing foreign matter included in the gas supplied from the gas supply source is inserted in the tube 2071. In this way, the gas having the foreign matter removed by the filter is supplied to the gas connector 2072. Further, a first sealing member 2073 having a ring shape is fit in a gap between the tip portion 2072*a* of the gas connector 2072 and an inner wall of the second recessed portion 2621*b*. In this way, a region surrounded by the tip portion 2072*a* of the gas connector 2072 and the inner wall of the second recessed portion 2621*b* is sealed. The cutting machining device 2001 according to the present modification example performs machining on a workpiece while ejecting gas supplied from the gas supply source toward a tip portion of the tool 20 via the nozzle 2623.

When the workpiece W is a bone, there is a risk that a cell of a machined portion may die when a temperature of the machined portion rises. In contrast, the present configuration can perform machining on the workpiece W while ejecting gas for cooling being ejected from the nozzle 2623 toward a portion where a machined portion of the workpiece W and the tool 20 are in contact. Therefore, an excessive temperature rise of the machined portion of the workpiece W can be suppressed, and thus damage to the workpiece W can be suppressed.

Figure 5:
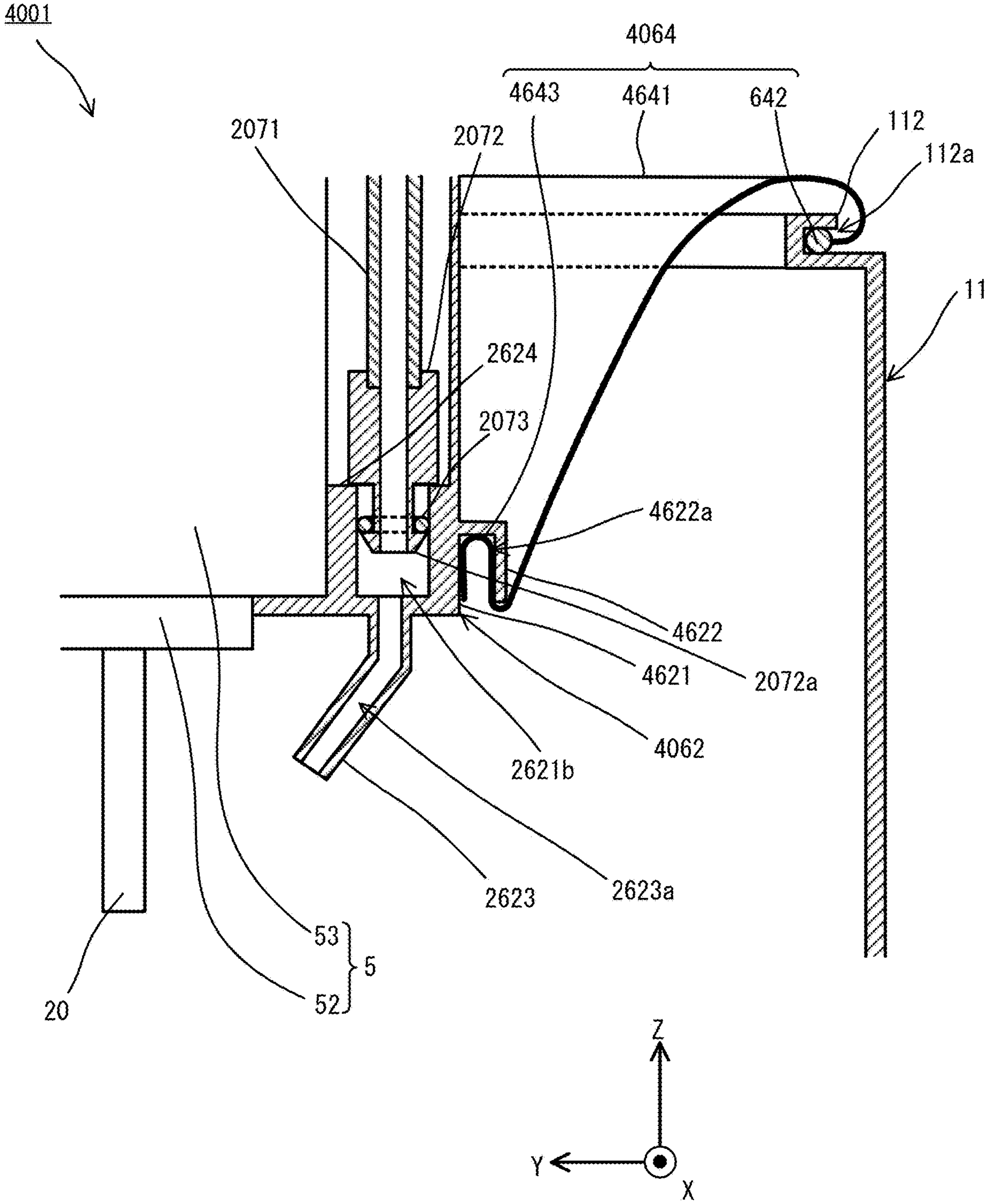
FIG. 5 is a cross-sectional view of a part of the cutting machining device according to the modification example.

Further, for example, as in a cutting machining device 4001 illustrated in FIG. 5, a second cover 4064 including a head-side fixed portion 4643 having a cross-sectional U-shape may be included. Note that, in FIG. 5, a configuration similar to that in the cutting machining device 2001 has the same reference sign as that in FIG. 4. A head cover 4062 includes a head cover main body 4621 having a bottomed tubular shape, and a sixth outer flange portion 4622 protruding from the head cover main body 4612 in a direction away from a tubular axis of the head cover main body 4621 in a direction orthogonal to a tubular axis direction of the head cover main body 4621. A second groove 4622*a* in which the head-side fixed portion 4643 of the second cover 4064 is fit is recessed toward the +Z direction side and formed in a surface on the −Z direction side of the entire sixth outer flange portion 4622. Then, the second cover 4064 is fixed to the head cover 4062 while the entire head-side fixed portion 4643 of a second cover main body 4641 is fit in the second groove 4622*a* of the sixth outer flange portion 4622. In the present modification example, the entire machining region S1 is in a positive pressure state with respect to the other region by supplying gas from the nozzle 2623 to the machining region S1 with the doors 14 in the close state, and the head-side fixed portion 4643 having the cross-sectional U-shape accordingly expands and is in close contact with an inner wall of the second groove 4622*a*. Note that the holding unit-side fixed portion 633 of the first cover 63 may also similarly have the cross-sectional U-shape. Further, the machining region S1 may be maintained in a positive pressure state by providing a membrane filter (not illustrated) in a part of the interior case 11 and supplying gas from the nozzle 2623 at all times.

The present configuration can increase a degree of sealing of the machining region S1 by increasing a degree of close contact of the head-side fixed portion 4643 of the second cover 4064 with the head cover 4062, and thus entry of foreign matter from the outside of the machining region S1 into the machining region S1 can be accordingly suppressed, and a degree of cleanliness of the machining region S1 can be increased.

Figure 6:
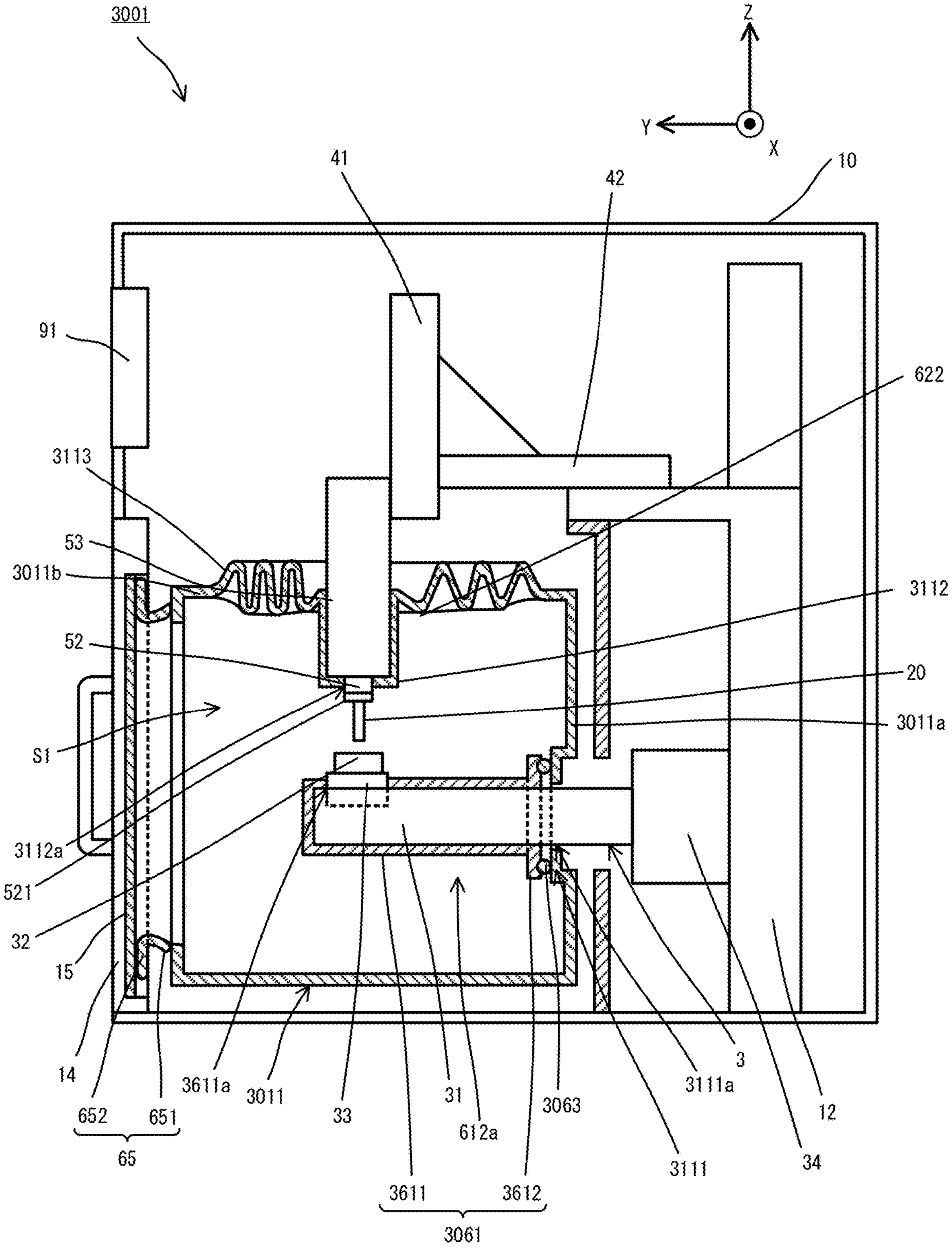
FIG. 6 is a cross-sectional view of the cutting machining device according to the modification example.

In the embodiment, the example in which the interior case 11, the head cover 62, the first cover 63, and the second cover 64 are different bodies is described. However, the present disclosure is not limited to this, and, for example, as in a cutting machining device 3001 illustrated in FIG. 6, an interior case 3011 that covers a part of the head 5 may be included. Herein, the interior case 3011 may correspond to the interior case 11, the head cover 62, the first cover 63, and the second cover 64 in the embodiment being continuously integrally formed. Note that, in FIG. 6, a configuration similar to that in the embodiment has the same reference sign as that in FIG. 2. The cutting machining device 3001 includes a holding unit cover 3061 and a second sealing member 3063 in addition to the interior case 3011. Further, an infrared sensor (not illustrated) for detecting a relative position of the head 5 with respect to the interior case 3011 is provided on the head main body 53 of the head 5.

The interior case 3011 has a box shape, and includes a protruding portion 3111 protruding from a side wall 3011*a* on the −Y direction side in the +Y direction and having a bottomed tubular shape, and a protruding portion 3112 protruding from a top wall 3011*b* on the +Z direction side toward the −Z direction side and having a bottomed tubular shape. The interior case 3011 is formed of an elastic material such as rubber and an elastomer, for example. A second holding unit insertion hole 3111*a* through which the holding unit 3 is inserted penetrates a bottom wall of the protruding portion 3111. Further, a part of the head main body 53 of the head 5 is fit inside the protruding portion 3112. Furthermore, a head insertion hole 3112*a* through which the main rotating shaft 52 of the head 5 fit inside the protruding portion 3112 is inserted penetrates a bottom wall of the protruding portion 3112. Further, a pleated portion 3113 is formed on the top wall 3011*b* in such a way as to concentrically surround a central axis as the center along a protruding direction of the protruding portion 3122 when viewed from a thickness direction of the top wall 3011*b*. Furthermore, a reflection plate (not illustrated) that reflects infrared light radiated from the infrared sensor provided on the head main body 53 is provided on a part of the bottom wall inside the protruding portion 3112.

The holding unit cover 3061 includes a holding unit cover main body 3611 having a bottomed square tubular shape, and a fifth outer flange portion 3612 protruding from the holding unit cover main body 3611 in a direction away from a tubular axis of the holding unit cover main body 3611 in a direction orthogonal to a tubular axis direction of the holding unit cover main body 3611. A third holding unit insertion hole 3611*a* through which a part of the workpiece holding unit 32 and the holding portion driver 33 of the holding unit 3 can be inserted is provided in a side wall of the holding unit cover main body 3611. The fifth outer flange portion 3612 is located on an end portion on a side opposite to a bottom wall side outside the side wall of the holding unit cover main body 3611. The holding unit cover 3061 is mounted on the holding unit 3 while a part of the workpiece holding unit 32 and the holding portion driver 33 of the holding unit 3 is inserted through the third holding unit insertion hole 3611*a*. Further, a surface of the fifth outer flange portion 3612 on the side opposite to the bottom wall side of the holding unit cover main body 3611 in the thickness direction is fixed to a surface on the +Y direction side of the protruding portion 3111 of the interior case 3011 via the second sealing member 3063.

Herein, a preparation method when cutting machining is performed on the workpiece W by using the cutting machining device 3001 according to the present modification example is described. First, with the doors 14 in the open state, the interior case 3011 is disposed in a preset fixed position inside the housing 10. At this time, the interior case 3011 is in a state of being locked by the locking portion of the housing 10. Next, by operating the control panel 91, and the head 5 is disposed in a position on the +Z direction side of the protruding portion 3112 of the interior case 3011. At this time, the cutting machining device 3001 performs positioning of the head 5, based on intensity of reflected light from the reflection plate disposed on the bottom wall inside the protruding portion 3112, by the above-described infrared sensor. Subsequently, when the head 5 is disposed on the +Z direction side of the protruding portion 3112 of the interior case 3011, the head 5 is lowered by operating the control panel 91. In this way, the main rotating shaft 52 of the head 5 is inserted through the head insertion hole 3112*a* of the interior case 3011, and the head main body 53 is fit inside the protruding portion 3112.

Then, the second sealing member 3063 and the holding unit cover 3061 are mounted on the unit main body 31 of the holding unit 3 in order. At this time, a part of the workpiece holding unit 32 and the holding portion driver 33 of the holding unit 3 is inserted through the third holding unit insertion hole 3611*a* of the holding unit cover 3061 and exposed to the outside of the holding unit cover 3061. Subsequently, the fifth outer flange portion 3612 of the holding unit cover 3061 is fixed to the protruding portion 3111 of the interior case 3011 via the second sealing member 3063. Next, after the protective panel 15 is disposed in such a way as to cover the window portion 10*a* of the housing 10, the doors 14 are brought into the close state, and then the protective panel 15 is fit in the first recessed portion 14*a* of the doors 14. In this way, preparation for performing cutting machining on the workpiece W is completed.

When the workpiece W is, for example, a bone, a machining scrap causing a risk of infection adheres to an inner wall of the interior case 3011 after cutting machining. Thus, the inside of the interior case 3011 is required to be carefully washed in order to prevent cross infection between patients particularly when cutting machining is performed on bones of a plurality of patients. Further, when the inside of the interior case 3011 is washed, there is also a risk that a worker who performs washing may contract a disease of a patient by inhaling a machining scrap adhering to the inner wall of the interior case 3011. In contrast, according to the present modification example, the number of parts needed to block the above-described machining region S1 is reduced further than that in the embodiment, and thus it accordingly becomes easy to wash, and time and effort required for washing are also reduced. Thus, a risk of infection caused by a machining scrap can be accordingly suppressed. Further, a risk of infection can be reduced by removing the interior case 3011 from the housing 10 and discarding the interior case 3011 as it is as infected waste.

In the embodiment, the example in which the interior case 11, the holding unit cover 61, and the head cover 62 are formed of metal is described, but a material forming these is not limited to metal. For example, each of the interior case 11, the holding unit cover 61, and the head cover 62 may be formed of resin. In this case, the interior case 11, the holding unit cover 61, and the head cover 62 can be reduced in weight, and thus the entire cutting machining device 1 can be reduced in weight. Further, in this case, the holding unit cover 61 and the head cover 62 may be bonded or welded to the interior case 11. Alternatively, the interior case 11, the holding unit cover 61, and the head cover 62 may be formed by solid casting. In this case, time and effort to mount the holding unit cover 61 and the head cover 62 on the interior case 11 can be eliminated.

In the embodiment, the surface of the interior case 11, the holding unit cover 61, the head cover 62, the first cover 63, the second cover 64, the protective panel 15, and the gasket 65 may be coated with a thin film of silicon nitride or a resin film containing fine particles of silicon nitride. In this way, a sterilization effect on the surface of the interior case 11, the holding unit cover 61, the head cover 62, the first cover 63, the second cover 64, the protective panel 15, and the gasket 65 can be increased.

In the embodiment, the doors 14 may be freely attachable and detachable with respect to the housing 10. In this case, the doors 14 can be removed from the housing 10, and washed or subjected to sterilization treatment, and thus workability of maintenance of the cutting machining device 1 can be increased.

Although the embodiments and the modification examples of the present disclosure have been described above, the present disclosure is not limited to them. The present disclosure includes the embodiments and the modification examples being appropriately combined and also the embodiments and the modification examples being appropriately added with modifications.

This application claims the benefit of Japanese Patent Application No. 2021-180982, filed on Nov. 5, 2021, the entire disclosure of which is incorporated by reference herein.

INDUSTRIAL APPLICABILITY

The present disclosure is suitable as a cutting machining device that performs cutting machining of a bone.

REFERENCE SIGNS LIST

1, 2001, 3001, 4001 Cutting machining device
3 Holding unit
5 Head
10 Housing
10*a* Window portion
11, 3011 Interior case
11*a* First opening
11*b* Second opening
11*c* Third opening
12 Support stage
14 Door
14*a* First recessed portion
15 Protective panel
20 Tool
31 Unit main body
32 Workpiece holding unit
33 Holding portion driver
34 Main body driver

41 Raising and lowering driver
42 Horizontal driver
52 Main rotating shaft
53 Head main body
61, 3061 Holding unit cover
62, 2062, 4062 Head cover
63 First cover
64, 4064 Second cover
65 Gasket
91 Control panel
111 First rib
112 Second rib
111*a* Third groove
112*a* Fourth groove
521 Tool holding portion
611, 3611 Holding unit cover main body
611*a* First holding unit insertion hole
612*a* First groove
621, 2621, 4621 Head cover main body
622*a*, 2622*a*, 4622*a* Second groove
631 First cover main body
641, 4641 Second cover main body
612 First outer flange portion
622 Second outer flange portion
621*a*, 2621*a*, 3112*a* Head insertion hole
632 First interior case-side fixed portion
633 Holding unit-side fixed portion
642 Second interior case-side fixed portion
643, 4643 Head-side fixed portion
651 Gasket main body
652 Third outer flange portion
2073 First sealing member
2621*b* Second recessed portion
3063 Second sealing member
2071 Tube
2072 Gas connector
2072*a* Tip portion
2622 Fourth outer flange portion
2623 Nozzle
2623*a* Inside
2624 Step portion
3011*a* Side wall
3011*b* Top wall
3111, 3112 Protruding portion
3111*a* Second holding unit insertion hole
3113 Pleated portion
3611*a* Third holding unit insertion hole
3612 Fifth outer flange portion
4622 Sixth outer flange portion
S1 Machining region
W Workpiece

The invention claimed is:

1. A cutting machining device comprising:

a head to which a tool is fixed;

a holding unit that is disposed to face the head, and configured to hold a workpiece;

an interior case having a box shape, and in a surrounding wall, a first opening through which the holding unit is inserted and a second opening through which the head is inserted, at least a portion of the holding unit for holding the workpiece and the tool held by the head being disposed inside the interior case;

a holding unit cover having a bottomed tubular shape, and, in a side wall, a holding unit insertion hole through which the portion of the holding unit for holding the workpiece is inserted, and being mounted on the holding unit while the portion of the holding unit for holding the workpiece is inserted through the holding unit insertion hole;

a head cover having a bottomed tubular shape, and, in a bottom wall, a head insertion hole through which a portion of the head for holding the tool is inserted, and being mounted on the head while the portion of the head for holding the tool is inserted through the head insertion hole;

a first cover that blocks between the holding unit cover and an outer circumferential portion of the first opening in the interior case; and a second cover that blocks between the head cover and an outer circumferential portion of the second opening in the interior case.

2. The cutting machining device according to claim 1, further comprising:

a housing having a box shape and a window portion on a part of a surrounding wall of the housing, and housing the head, the holding unit, the interior case, the holding unit cover, the head cover, the first cover, and the second cover;

a door that is attached to an outer circumferential portion of the window portion in the surrounding wall of the housing in such a way as to be freely opened and closed, and is configured to be brought into a closed state of covering the window portion and an open state of leaving the window portion open;

a protective panel disposed in such a way as to cover the window portion between the interior case and the door; and a gasket that is formed of an elastic material in a ring shape, includes a first end portion in a tubular axis direction being fixed to a surface of the protective panel on a side opposite to a door side, and includes a second end portion being in contact with an outer wall of the interior case when the door is in the closed state, wherein the interior case has a third opening in a portion of the surrounding wall of the interior case facing the window portion while the interior case is disposed in the housing, and, when the protective panel is disposed in such a way as to cover the window portion between the interior case and the door, and the door is in the closed state, the entire second end portion of the gasket is in contact with an outer circumferential portion of the third opening in the surrounding wall of the interior case.

3. The cutting machining device according to claim 2, wherein the interior case, the holding unit cover, the head cover, the first cover, and the second cover are freely attachable and detachable with respect to the housing.

4. The cutting machining device according to claim 3, wherein a first groove extending around a tubular axis in an outside of the side wall is formed in the holding unit cover, a second groove is formed extending around the tubular axis in an outside of a side wall of the head cover, the interior case includes:

a first rib that has a tubular shape, protrudes from an outer circumferential portion of the first opening in the surrounding wall of the interior case toward an inside of the interior case, and has a third groove extending along a circumferential direction in the outer wall; and a second rib that has a tubular shape, protrudes from an outer circumferential portion of the second opening in the surrounding wall of the interior case toward an outside of the interior case, and has a fourth groove extending along a circumferential direction in the outer wall, the first cover has a tubular shape, includes a first end portion in a tubular axis direction being fit in the first groove of the holding unit cover, and includes a second end portion in the tubular axis direction being fit in the third groove of the interior case, and the second cover has a tubular shape, includes a first end portion in a tubular axis direction being fit in the second groove of the head cover, and includes a second end portion in the tubular axis direction being fit in the fourth groove of the interior case.

5. The cutting machining device according to claim 2, wherein a first groove extending around a tubular axis in an outside of the side wall is formed in the holding unit cover, a second groove is formed extending around the tubular axis in an outside of a side wall of the head cover, the interior case includes:

a first rib that has a tubular shape, protrudes from an outer circumferential portion of the first opening in the surrounding wall of the interior case toward an inside of the interior case, and has a third groove extending along a circumferential direction in the outer wall; and a second rib that has a tubular shape, protrudes from an outer circumferential portion of the second opening in the surrounding wall of the interior case toward an outside of the interior case, and has a fourth groove extending along a circumferential direction in the outer wall, the first cover has a tubular shape, includes a first end portion in a tubular axis direction being fit in the first groove of the holding unit cover, and includes a second end portion in the tubular axis direction being fit in the third groove of the interior case, and the second cover has a tubular shape, includes a first end portion in a tubular axis direction being fit in the second groove of the head cover, and includes a second end portion in the tubular axis direction being fit in the fourth groove of the interior case.

6. The cutting machining device according to claim 5, wherein the first cover includes:

a first cover main body formed in a tubular shape;

a first interior case-side fixed portion that is formed in a ring shape, is continuously integrally formed with an entire first end portion of the first cover main body in a tubular axis direction of the first cover main body, and is fit in the first groove; and a holding unit-side fixed portion that is formed in a ring shape, is continuously integrally formed with an entire second end portion of the first cover main body in the tubular axis direction of the first cover main body, and is fit in the third groove, and the second cover includes:

a second cover main body formed in a tubular shape;

a second interior case-side fixed portion that is formed in a ring shape, is continuously integrally formed with an entire first end portion in a tubular axis direction of the second cover main body, and is fit in the second groove; and a head-side fixed portion that is formed in a ring shape, is continuously integrally formed with an entire second end portion in the tubular axis direction of the second cover main body, and is fit in the fourth groove.

7. The cutting machining device according to claim 5, wherein the first cover includes:

a first cover main body formed in a tubular shape;

a first interior case-side fixed portion that is formed in a ring shape, is continuously integrally formed with an entire first end portion of the first cover main body in a tubular axis direction of the first cover main body, and is fit in the first groove; and a holding unit-side fixed portion that is formed in a ring shape, is continuously integrally formed with an entire second end portion of the first cover main body in the tubular axis direction of the first cover main body, and is fit in the third groove, and the second cover includes:

a second cover main body formed in a tubular shape;

a second interior case-side fixed portion that is formed in a ring shape, is continuously integrally formed with an entire first end portion in a tubular axis direction of the second cover main body, and is fit in the second groove; and a head-side fixed portion that is formed in a ring shape, is continuously integrally formed with an entire second end portion in the tubular axis direction of the second cover main body, and is fit in the fourth groove.

8. The cutting machining device according to claim 1, wherein a first groove extending around a tubular axis in an outside of the side wall is formed in the holding unit cover, a second groove is formed extending around the tubular axis in an outside of a side wall of the head cover, the interior case includes:

a first rib that has a tubular shape, protrudes from an outer circumferential portion of the first opening in the surrounding wall of the interior case toward an inside of the interior case, and has a third groove extending along a circumferential direction in the outer wall; and a second rib that has a tubular shape, protrudes from an outer circumferential portion of the second opening in the surrounding wall of the interior case toward an outside of the interior case, and has a fourth groove extending along a circumferential direction in the outer wall, the first cover has a tubular shape, includes a first end portion in a tubular axis direction being fit in the first groove of the holding unit cover, and includes a second end portion in the tubular axis direction being fit in the third groove of the interior case, and the second cover has a tubular shape, includes a first end portion in a tubular axis direction being fit in the second groove of the head cover, and includes a second end portion in the tubular axis direction being fit in the fourth groove of the interior case.

9. The cutting machining device according to claim 8, wherein the first cover includes:

a first cover main body formed in a tubular shape;

a first interior case-side fixed portion that is formed in a ring shape, is continuously integrally formed with an entire first end portion of the first cover main body in a tubular axis direction of the first cover main body, and is fit in the first groove; and a holding unit-side fixed portion that is formed in a ring shape, is continuously integrally formed with an entire second end portion of the first cover main body in the tubular axis direction of the first cover main body, and is fit in the third groove, and the second cover includes:

a second cover main body formed in a tubular shape;

a second interior case-side fixed portion that is formed in a ring shape, is continuously integrally formed with an entire first end portion in a tubular axis direction of the second cover main body, and is fit in the second groove; and a head-side fixed portion that is formed in a ring shape, is continuously integrally formed with an entire second end portion in the tubular axis direction of the second cover main body, and is fit in the fourth groove.

* * * * *